US009138167B1

(12) United States Patent
Leydon

(10) Patent No.: US 9,138,167 B1
(45) Date of Patent: Sep. 22, 2015

(54) MEANS FOR RENDERING KEY RESPIRATORY MEASUREMENTS ACCESSIBLE TO MOBILE DIGITAL DEVICES

(76) Inventor: Krispin Johan Leydon, La Canada Flintridge, CA (US)

(*) Notice: Subject to any disclaimer, the term of this patent is extended or adjusted under 35 U.S.C. 154(b) by 630 days.

(21) Appl. No.: 12/924,245

(22) Filed: Sep. 22, 2010

Related U.S. Application Data

(60) Provisional application No. 61/246,058, filed on Sep. 25, 2009.

(51) Int. Cl.
*A61B 5/087* (2006.01)

(52) U.S. Cl.
CPC ..................... *A61B 5/087* (2013.01)

(58) Field of Classification Search
CPC .... A61B 5/087; A61B 5/0871; G01F 1/3236; G01F 1/3209; G01F 1/32; G01F 1/3263; G01P 5/00
USPC .................. 600/529, 538; 73/861.19, 861.21, 73/861.23, 861.25, 861.355, 861.32; 128/203.12; 446/202, 204, 206; 116/147; 340/404.1–404.3
See application file for complete search history.

(56) References Cited

U.S. PATENT DOCUMENTS

| | | | |
|---|---|---|---|
| 2,794,341 A * | 6/1957 | Vonnegut | 73/861.32 |
| 3,367,324 A | 2/1968 | De Bono | |
| 3,473,377 A * | 10/1969 | Reinecke | 73/861.34 |
| 3,714,828 A | 2/1973 | Durkan | |
| 4,182,172 A | 1/1980 | Wennberg et al. | |
| 4,244,212 A * | 1/1981 | Stignani | 73/112.01 |
| 4,930,357 A | 6/1990 | Thurston et al. | |
| 5,003,828 A * | 4/1991 | van den Burg | 73/861.33 |
| 5,363,842 A * | 11/1994 | Mishelevich et al. | 128/200.14 |
| 5,518,002 A * | 5/1996 | Wolf et al. | 600/538 |
| 5,732,709 A | 3/1998 | Tacklind et al. | |
| 5,864,067 A | 1/1999 | Ligneul et al. | |
| 6,289,313 B1 | 9/2001 | Heinonen et al. | |
| 6,968,375 B1 | 11/2005 | Brown | |
| 7,063,669 B2 * | 6/2006 | Brawner et al. | 600/533 |

(Continued)

OTHER PUBLICATIONS

Hiroshi Sato, et al. "Application of the Vortex Whistle to the Spirometer", 1999, Transactions of the Society of Instrument and Control Engineers, p. 840-845, V35, N7, Japan.

(Continued)

*Primary Examiner* — Patricia Mallari
*Assistant Examiner* — Michael Catina
(74) *Attorney, Agent, or Firm* — The Marbury Law Group, PLLC

(57) ABSTRACT

An acoustic means for rendering key respiratory measurements accessible to hand-held mobile digital devices with audio input capabilities (such as mobile phones, personal digital assistants, mobile gaming platforms, and tablets). One or more embodiments comprise: a compact and portable whistle (101) that encodes a user's expiratory airflow rate as audio frequency, and a software process with local or remote access to mobile-device audio that decodes said audio frequency to regain expiratory airflow rate and derive key respiratory measurements, so that these measurements and related information may conveniently be made available to the user (100) and the user's health network of family members (103) and physicians (104). Embodiments enable leveraging the ubiquity and extensive capabilities of hand-held mobile digital devices, while simultaneously simplifying requirements for a dedicated spirometry device.

10 Claims, 5 Drawing Sheets

(56) References Cited

U.S. PATENT DOCUMENTS

| | | |
|---|---|---|
| 7,093,501 B2 * | 8/2006 | Kuo et al. ............... 73/861.23 |
| 7,094,208 B2 | 8/2006 | Williams et al. |
| 7,264,591 B2 | 9/2007 | Brown |
| 7,383,740 B2 | 6/2008 | Krasilchikov et al. |
| 8,109,266 B2 * | 2/2012 | Addington et al. ...... 128/203.12 |
| 2005/0183725 A1 | 8/2005 | Gumaste |
| 2006/0206036 A1 * | 9/2006 | Quinn ..................... 600/538 |
| 2006/0253045 A1 | 11/2006 | Coifman |
| 2007/0179347 A1 * | 8/2007 | Tarassenko et al. ........ 600/300 |
| 2009/0084380 A1 * | 4/2009 | Gieschen et al. ........ 128/203.15 |
| 2009/0112114 A1 | 4/2009 | Ayyagari |
| 2009/0270751 A1 | 10/2009 | Peng et al. |
| 2009/0314292 A1 * | 12/2009 | Overfield et al. ........ 128/203.15 |

OTHER PUBLICATIONS

H. Sato and K. Watanabe, "Experimental Study on the Use of a Vortex Whistle as a Flowmeter," IEEE Transactions on Instrumentation and Measurement, vol. 49, No. 1, Feb. 2000, pp. 200-205.

T. Togawa, T. Tamura and P. A. Oberg, Excerpt from "Biomedical Transducers and Instruments," CRC Press, May 21, 1997, pp. 162-164.

R. C. Chanaud, "Experiments Concerning the Vortex Whistle," J. Acoust. Soc. Amer., vol. 37, No. 7, pp. 953-960, 1963.

B. Vonnegut, "A Vortex Whistle," J. Acoust. Soc. Amer., vol. 26, No. 1, pp. 18-20, 1954.

\* cited by examiner

Fig. 7
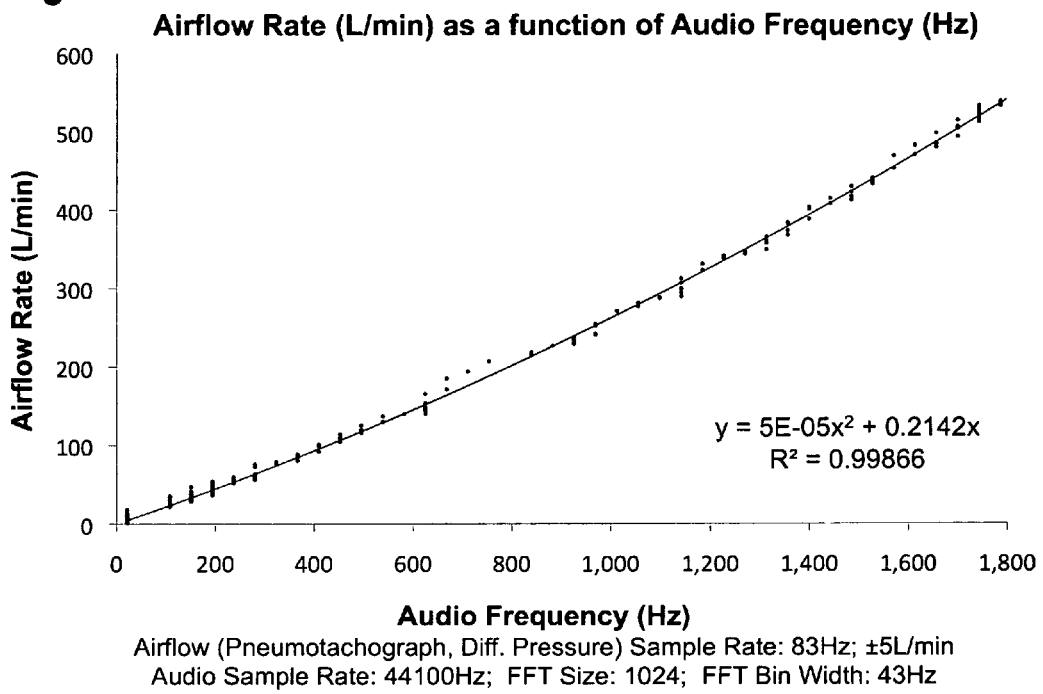
Airflow (Pneumotachograph, Diff. Pressure) Sample Rate: 83Hz; ±5L/min
Audio Sample Rate: 44100Hz; FFT Size: 1024; FFT Bin Width: 43Hz
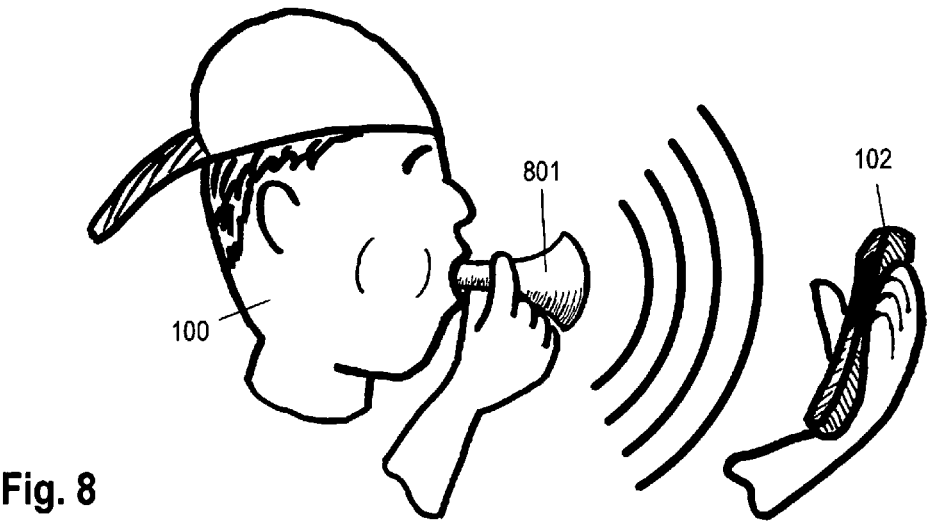
Fig. 8

MEANS FOR RENDERING KEY RESPIRATORY MEASUREMENTS ACCESSIBLE TO MOBILE DIGITAL DEVICES

CROSS-REFERENCE TO RELATED APPLICATIONS

This application claims the benefit of provisional patent application Ser. No. 61/246,058, filed 2009 Sep. 25 by the present inventor.

FEDERALLY SPONSORED RESEARCH

Not Applicable

SEQUENCE LISTING OR PROGRAM

Not Applicable

BACKGROUND

1. Field

This application concerns human expiratory airflow measurement and monitoring through the use of portable devices and systems.

2. Prior Art

Spirometers—devices that monitor respiration—are used in range of clinical, domestic, and vocational situations. Spirometers are used to diagnose and monitor common respiratory conditions such as asthma and chronic obstructive pulmonary disease (COPD), screen for occupational health hazards such as silicosis and black lung disease, and assist athletes and lung transplant recipients to monitor lung performance.

There are two general categories of spirometers—diagnostic spirometers and monitoring spirometers—each with its own set of requirements. Diagnostic spirometers are used in clinical settings, and must measure a number of respiratory parameters with high accuracy and precision. Monitoring spirometers are more frequently used in domestic and vocational settings; they must be cost-effective for individual users, compact, convenient, robust, low-maintenance, and designed for routine use.

Monitoring spirometers typically measure a person's peak expiratory flow rate (PEF, or PEFR), defined as the maximum volumetric airflow rate recorded during a voluntary forced expiration of air from the lungs. In addition to PEFR, another parameter measured by some monitoring spirometers is one-second forced expiratory volume ($FEV_1$): the volume of air a person can forcibly exhale over the course of one second following a deep inhalation. (The subscript in this abbreviation indicates the duration of exhalation, in seconds.) Portable, compact monitoring spirometers that enable a user to monitor peak expiratory flow rate are commonly referred to as "peak flow monitors". Peak flow monitors that facilitate measurement of peak expiratory flow are commonly referred to as "peak flow meters".

Peak flow meters hold particular promise in the domain of asthma management. Asthma's prevalence world-wide has increased by approximately 50% per decade in recent history, and according to the World Health Organization (WHO), the human and economic burden associated with asthma surpasses that of AIDS and tuberculosis combined (2006). Approximately 300 million people world-wide suffer from asthma, and each year asthma results in over 200,000 deaths (International Union against Tuberculosis and Lung Disease, 2005). In America alone, asthma affects 20 million people, and accounts for $14 billion in health expenditures and lost productivity each year. Asthma is the most common chronic illness among children (National Institute of Health, 2006).

Asthma is a considerable problem, and peak flow meters play a role in the asthma management strategies that physicians and medical institutions recommend. According to the National Institute of Health (NIH): "A peak flow meter can tell you when an episode is coming—even before you feel the symptoms. Taking medicine before you feel symptoms can stop the episode. People over the age of 4 with moderate or severe asthma should use a peak flow meter at least daily" (NIH Publication No. 91-2664). The "Pocket Guide to Asthma Management" (2004) published by the Global Initiative for Asthma (GINA) recommends that patients monitor peak flow "as much as possible". The National Asthma Education Program's (NAEP) 2007 Expert Panel Report highlights the value of regular PEFR readings in evaluating medications, detecting "early warning" signs, and precluding hospital visits (NIH Publication No. 07-4051). The American Thoracic Society (ATS) and National Heart, Lung and Blood Institute (NHLBI) recommend that patients with known respiratory disease regularly monitor their lung function. When a patient is able to routinely monitor his/her condition, the chances of successful management are improved.

Despite the recommendations of medical authorities, use of peak flow meters is far from ubiquitous. According to Allan H. Goroll, M D and Albert G. Mulley, M D, authors of the 2009 edition of "Primary Care Medicine", only 20% of asthma patients who stand to benefit from using a peak flow meter actually use one. In practice, availability, adoption and adherence all strongly influence the impact that existing monitoring solutions have on asthma management outcomes worldwide.

While leading physicians and medical institutions are encouraging self-care through routine peak airflow monitoring, they are not recommending that the entire burden of asthma management fall on the shoulders of individual patients. Rather, medical authorities such as the NAEP are advocating for a network-based approach to self-care, characterized by collaborative relationships between patients, physicians and family members. Within such a network-based approach, the timely sharing of health information among concerned parties is of particular importance.

There are several classes of peak flow monitoring devices. One early type of device renders a threshold expiratory airflow perceptible to end-users by means of a whistle. If the whistle sounds when the user blows into the device, the user is meant to conclude that their peak airflow is above this threshold airflow rate. The threshold can be adjusted, usually by enlarging or contracting a leak orifice situated between a mouthpiece and the whistle section of the device. The leak orifice diverts a portion of incoming airflow so that this portion does not pass through the whistle. While such devices are inexpensive, simple to use, and reward their users sonically for exhaling as forcefully as possible, their threshold values must be set properly prior to use in order to achieve valid results. Furthermore, as threshold devices, they do not facilitate routine measurement in the manner that leading physicians and medical institutions now recommend.

The majority of peak flow meters currently available are mechanical devices with an enclosed moving element (such as a piston) connected to an externally visible pointer, positioned in close relation to a measurement scale. When a user blows into such a device, the force of his/her breath repositions the moving element, and its associated pointer points to a location on the measurement scale to indicate the user's peak expiratory flow. While such mechanical peak flow meters are simple and relatively inexpensive, friction, inertia, gravity, and other artifacts of mechanical implementation can compromise their accuracy. The need for at least one enclosed moving part has implications for reliability, ease of cleaning, and ease of sterilization. Since mechanical peak flow meters typically only display the result of the most recent measurement trial, they do not facilitate presentation of multiple trial results simultaneously—much less the visualization or exploration of trial data over a range of time scales.

In response to some of the limitations of threshold-whistle monitors and mechanical peak flow meters, electronic peak flow meters have been devised. Electronic peak flow meters typically incorporate some form of sensor, microprocessor, non-volatile memory and an LCD display. Approaches to sensing vary; some devices sense the rate at which a rotor spins in response to breath-generated airflow. Other devices sense a difference in pressure between two points along an air passageway, or the extent of Doppler shift in an ultrasound signal as it passes across an air passageway. Sensed values are usually translated into peak airflow rate values by a microprocessor, stored in non-volatile memory, and presented on an LCD display for a user to view. Electronic peak flow meters tend to be more accurate than their mechanical counterparts, and are able to store and display measurements (in some cases, $FEV_1$ in addition to PEFR) from multiple trials. Some electronic peak flow meters also have the capability of sending measurement data to a personal computer via an attached cable or a wireless (radio-wave based) connection.

Although electronic peak flow meters typically offer greater measurement accuracy than mechanical peak flow meters, this accuracy comes at a price. Electronic peak flow meters tend to be significantly more expensive, and are also frequently less intuitive to use. To keep manufacturing costs down, user interface elements (buttons and LCD display symbols, symbol-sections and or pixels) are usually kept to a minimum—a factor that restricts ease of use. The electronic communication capabilities that some electronic peak flow meters offer are basic, and typically only possible with significant additional expense in the form of data cables, memory cards and personal computer software. Significantly, electronic peak flow meters do little at present to capitalize on advantages that software applications can provide within mobile contexts of use.

Electronic peak flow meters currently require batteries, and can run out of energy at inopportune moments—further eroding ease of use and reliability. The need for battery-powered electronics restricts how easily electronic peak flow meters can be washed and sterilized without risk of damage. While electronic peak flow meters are frequently sufficiently portable, they can become yet another battery-powered electronic device a patient must carry around on their person. In comparison with alternatives, electronic peak flow meters are more complex to manufacture and more difficult to recycle. They regularly contain toxic materials incongruous with their function as health-monitoring devices.

One interesting class of airflow sensor that has only been cursorily explored in the context of spirometry so far is that of the vortex whistle. Vortex whistles have the property that the fundamental frequency of sound waves they emit varies reliably and repeatably with the rate of fluid flow passing through them. This property makes it possible to derive a vortex whistle's through-passing airflow rate from its frequency emissions. Vortex whistles were first characterized by Bernard Vonnegut at General Electric Research Laboratory during the 1950s, and their principle of operation explained within his 1954 article "A Vortex Whistle", published by the Journal of the Acoustic Society of America (Volume 26, Number 1). Essentially, a vortex whistle channels flowing fluid (liquid or gas) into a swirling vortex, and then through an outlet tube. As the vortex exits the outlet tube, it becomes unstable, and whips around with an angular velocity comparable to its rotational velocity. It is believed that the instability of the vortex as it exits the outlet tube creates the vortex whistle's sound.

To date, vortex whistles have been used primarily within the domain of industrial process control. The present research has uncovered one effort to apply the principle of the vortex whistle within the domain of spirometery, documented in "Application of the Vortex Whistle to the Spirometer" by Hiroshi Sato, et al. in Japan's 1999 Transactions of the Society of Instrument and Control Engineers. This effort employed a vortex whistle based on Vonnegut's design to measure expiratory airflow rate on a desktop computer equipped with a microphone. While this investigation introduced the use of a vortex whistle for measurement of expiratory airflow rate, it did not address how the design of a vortex whistle could be refined for use within the context of a portable monitoring spirometry solution, nor did it consider or address mobile scenarios of use.

In addition to vortex flow whistles, other forms of fluidic oscillators/fluidic whistles (devices that generate accoustic oscillation solely through their static structure and fluid dynamic interactions) have been considered within the context of spirometry, as evident from U.S. Pat. No. 3,714,828 (1973), U.S. Pat. No. 4,182,172 (1980), U.S. Pat. No. 7,0940, 208 (2006), and U.S. Pat. No. 7,383,740 (2008). The spirometry solutions put forward by these patents share the advantage of minimal need for calibration. Because, however, these solutions employ fluidic oscillators as components within or attached to dedicated electronic peak flow measurement devices or systems, they suffer from many of the previously discussed limitations that are typical of electronic peak flow meters. Furthermore, the solutions presented within these patents do not capitalize on audio feedback as a means to reward a user for exhaling as forcefully as possible.

While a range of monitoring spirometry solutions exists, there remains significant room for improvement, particularly in the following areas:

Communication: At present, peak flow meters are predominantly stand-alone devices that do little or nothing to support timely, convenient flow of health information throughout a patient's network of family members and physicians. In an age when networked mobile information services are commonplace, the lack of convenient mobile connectivity and structured channels of digital communication are notable shortcomings.

Visualization: Existing portable monitoring spirometry solutions frequently fail to provide concise graphical reports designed to facilitate quick, sound interpretation and effective medical treatment decisions. Furthermore, the user interfaces for existing portable monitoring solutions do little to support exploration of trends over multiple timescales.

Ease of Use: Existing monitoring solutions currently fail to minimize the inconvenience of routine monitoring regimens—not only for patients, but also for family members and physicians.

Annotation: Existing peak flow monitoring devices for the most part do not assist patients to supplement automated quantitative measurement with self-reported contextual details. The ability to annotate a trial record with information such as whether the trial was performed following medication, what medication(s) were used, and other information pertaining to the trial would be of value in subsequent reviews of trial data by patients, physicians and family members.

Motivation: Operation of a peak flow meter is effort-dependent. If a patient does not routinely exhale as forcefully as they are able, the most precise of measurement solutions cannot ensure accurate results. Contemporary solutions do little to reward the consistent effort required for routine expiratory airflow measurement—nor do they frame the activity of measurement in ways that invite enjoyment. Present solutions typically frame peak flow measurement as a task to be completed, when it could alternatively be framed as a game to be played, a competition to be won, or the price of admission for some other form of rewarding experience administered in periodic installments.

Social Acceptability: The aesthetic/industrial design of available peak flow monitoring devices is usually clinical and utilitarian; for the most part, available devices and systems cannot easily be construed as fun, cool, elegant or fashionable. If an asthma patient feels reluctant or embarrassed to carry, hold or use a monitoring solution, it is of little value to them.

Correlation: Identifying the factors that exacerbate symptoms is a significant aspect of asthma management. Existing portable peak flow monitoring solutions do little to help patients correlate their own lung function with a range of potentially relevant environmental variables, such as local pollen count and geographic location. The ability to facilitate correlation could be beneficial not only for patients and their networks, but also for public health and medical research institutions in their efforts to understand asthma on a larger scale.

Reminding: The vast majority of monitoring solutions do not provide patients with the option of configuring and activating automated reminders that could support the routine monitoring regimens that medical authorities recommend.

Although the frequently-competing constraints of low cost, accuracy and reliability have been considered in the past, these constraints have not historically been balanced in ways that leverage the mobile technologies that a growing number of people carry on their persons.

SUMMARY

In accordance with one or more embodiments, a means for making human expiratory airflow-related measurements accessible to hand-held mobile digital devices with audio input (such as mobile phones, personal digital assistants, mobile gaming platforms, and tablets) in a manner that is rapid, convenient, wireless, battery-less, and without need for manual recording or data entry.

One or more embodiments comprise: 1) A compact, portable whistle that continuously encodes a user's expiratory airflow rate as an audible frequency. 2) A software process that decodes the audible frequency to regain expiratory airflow rate, and derives respiratory parameters that are based on expiratory airflow rate, such as PEFR and $FEV_1$. The software process may run on the mobile device; alternatively it may run remotely on a network having access to audio from the mobile device, or it may be run in a distributed fashion: partially on the mobile device, and partially on the network.

An aspect of one or more embodiments is the ability to leverage certain advantageous aspects of hand-held mobile digital devices, while simultaneously simplifying requirements for a dedicated portable spirometry device. These advantageous aspects include: Connectivity for inter-personal communications and data transfer; reminding through audio, vibrotactile and graphical means; information display through sophisticated graphical, audio and vibrotactile means; manual control through buttons and/or touch screens; interactive feedback for motivational, instructional, editorial, aesthetic and enjoyment purposes; data recording, processing and storage; juxtaposition, combination and correlation of information from local and remote sources; configurability and extensibility in terms of the ability to download and incorporate additional/alternate sounds, graphics, animations and software applications.

Another aspect of one or more embodiments is the enabling of a spirometry solution with no moving parts, electronics or batteries, beyond what is already contained within the mobile device. (Numerous people already own and carry such mobile devices for purposes that are independent of spirometry). Since one or more variations of the whistle contain no moving parts, electronics or batteries, they can be manufactured and recycled more easily, cheaply and reliably than existing spirometers using fewer energy and material resources, can be manufactured from just one material, and can be made from material(s) that do not place the entryway of a user's respiratory and digestive tracts in close proximity with toxins during use.

Still another aspect of one or more embodiments is to make use of a whistle that produces sound wave emissions with a fundamental frequency that varies with airflow rate, for the purpose of communicating airflow-based measurements to a physically separate hand-held mobile digital device with audio input, a device that is not primarily designed for spirometry.

According to yet another aspect of one or more embodiments, respiratory measurements are made accessible to the hand-held mobile digital device through a means that is wireless, does not require initial configuration of a wireless network, and does not require any energy additional to the energy already contained within a user's forced exhalation.

Further aspects of one or more embodiments are that the whistle requires no frequent calibration, and can easily be cleaned and sterilized using aqueous solutions (such as detergent and water) without risk of damage.

According to a still further aspect of one or more embodiments, the whistle provides audible real-time feedback to a user that varies with a user's expiratory airflow rate. Measurement of forced expiration is effort-dependent, and audible feedback is one means of rewarding effort. In addition to rewarding user effort, audible feedback can also facilitate identifying and discounting invalid measurement trials.

According to an additional aspect of one or more embodiments, the range of frequencies that the whistle emits in response to peak expiratory airflow rates can fit comfortably within a frequency range suitable for both the microphones used in hand-held mobile digital devices, as well as one or more of the wireless networks to which such hand-held mobile digital devices can typically connect. The whistle's ability to function within a frequency range defined by these two requirements enables respiratory measurements to be derived by variations of the software process running locally on the hand-held mobile digital device, as well as by variations of the software process running remotely on another device that connects to a network to which the hand-held mobile digital device can connect.

According to yet another aspect of one or more embodiments, the geometry of the whistle aligns the direction of incoming airflow with the direction of outgoing airflow. This alignment assists a user to aim (and feel like they are aiming)

at the hand-held mobile digital device, permits the user to easily view interactive graphical feedback from the device, and supports reliable communication between the whistle and the mobile digital device.

These and other aspects of embodiments of the present invention can be more fully understood when read in conjunction with the following description, appended claims and accompanying drawings. While the drawings and description include numerous specificities, the present invention is broad in scope and intended to be limited as only set forth in the appended claims.

DRAWINGS

Figures

FIG. 7 shows an experimentally derived plot of the characteristic relationship between input airflow rate and output audio frequency for a prototype whistle, in accordance with an embodiment of the whistle illustrated in FIG. 2.

FIG. 8 depicts a user blowing through a whistle with a horn-shaped exterior towards a hand-held mobile digital device, in accordance with one or more embodiments.

REFERENCE NUMERALS

100—system's user, also referred to as the patient
101—whistle
102—hand-held mobile digital device
103—family members
104—physician
105—networked data processing, storage and communication resource
106—networked computer or mobile device, primarily used by a patient's family member(s)
107—networked computer or mobile device, primarily used by a patient's physician(s)
200—inlet
201—airflow guide
201B—rounded front face of airflow guide's center (visible in FIG. 6)
201C—front face of an airflow guide's vane (one of 8 vanes visible in FIG. 6)
202—main tube
203—airflow constrictor ring
204—outlet tube
205—outlet
801—whistle with a musical horn-like exterior
900—housing for an inhaler-dispenser, also referred to as a medical dosage dispenser
901—medicine container
902—whistle
903—mouthpiece
1000—medicine delivery channel
1001—medicine container's nozzle
1002—outlet
3000 . . . 3140—stages in a software process

DETAILED DESCRIPTION

FIGS. 1,2,3,4,5,6,7—First Embodiment

Figure 1:
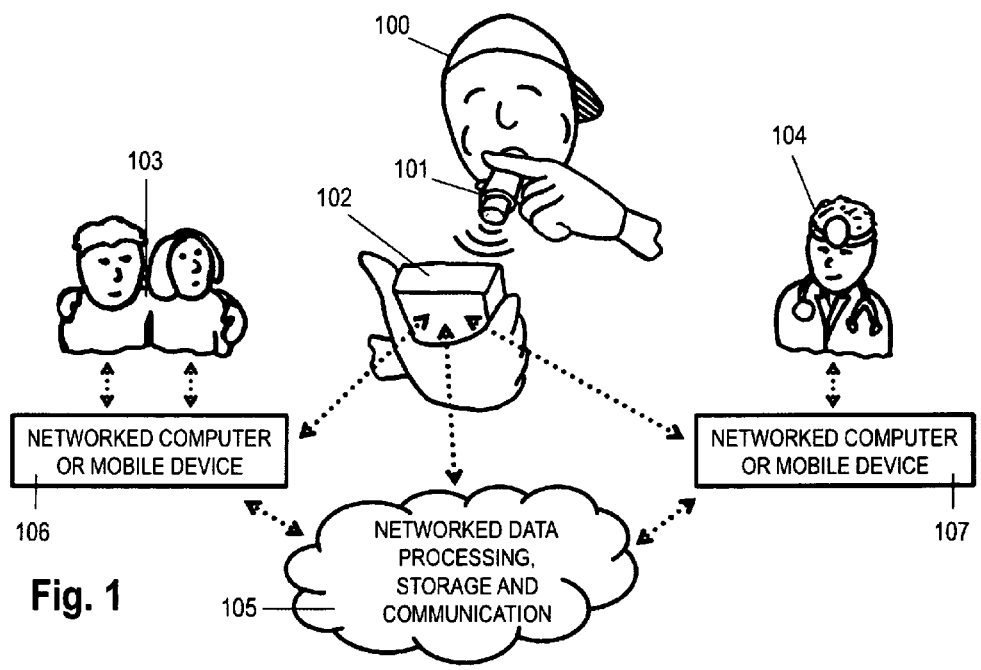
FIG. 1 shows a system diagram in accordance with one or more embodiments.

FIG. 1 illustrates the system surrounding and including one or more embodiments of the present invention. This system diagram depicts a user 100, and a whistle 101 that, when blown through forcefully by a user, emits sound waves whose fundamental frequency varies with the user's expiratory airflow rate in a reliable and repeatable manner. FIG. 1 additionally depicts hand-held mobile digital device 102 with a microphone, a display, the capability of running the software process described in FIG. 3, and the ability to communicate data (including audio data) over at least one wireless network. Family members 103 and a physician 104 represent the user's asthma care network. A networked data processing, storage and communication resource 105, and computers or mobile devices owned and or operated by one or more family member(s) and physician(s) (106,107) are also depicted.

Figure 2:
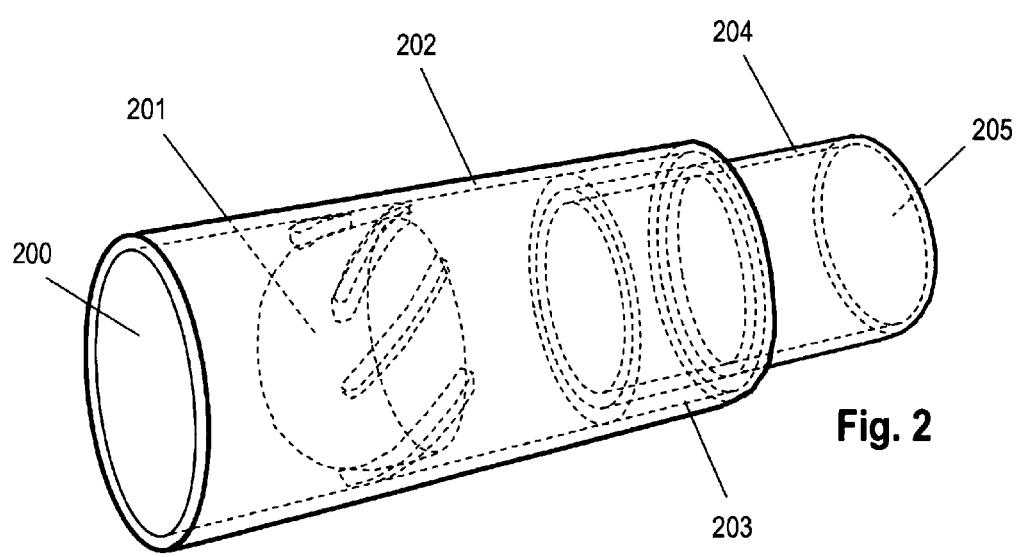
FIG. 2 shows a perspective view of a whistle, in accordance with one or more embodiments.

FIG. 2 illustrates a whistle that is part of one or more embodiments of the present invention. The whistle has an inlet 200 and an outlet 205. Situated between inlet and outlet within the whistle's hollow main tube 202, there is an airflow guide 201. The airflow guide, together with the inner wall of the main tube, define several airflow passageways. The section of the whistle's main tube stretching from the inlet to the airflow guide can alternately be referred to as the inlet-region of the main tube, the inlet tube, or the mouthpiece. An airflow constrictor ring, 203, creates a transition between the main tube and an outlet tube, 204, the outlet tube being of decreased diameter. The cylindrical cavity within the main tube between the airflow guide and the outlet tube can be referred to as the central cavity. Because the inlet tube and outlet tube within this variation of the whistle are coaxially aligned, the net direction of airflow into the whistle is substantially the same as the net direction of airflow out of the whistle.

Figure 3:
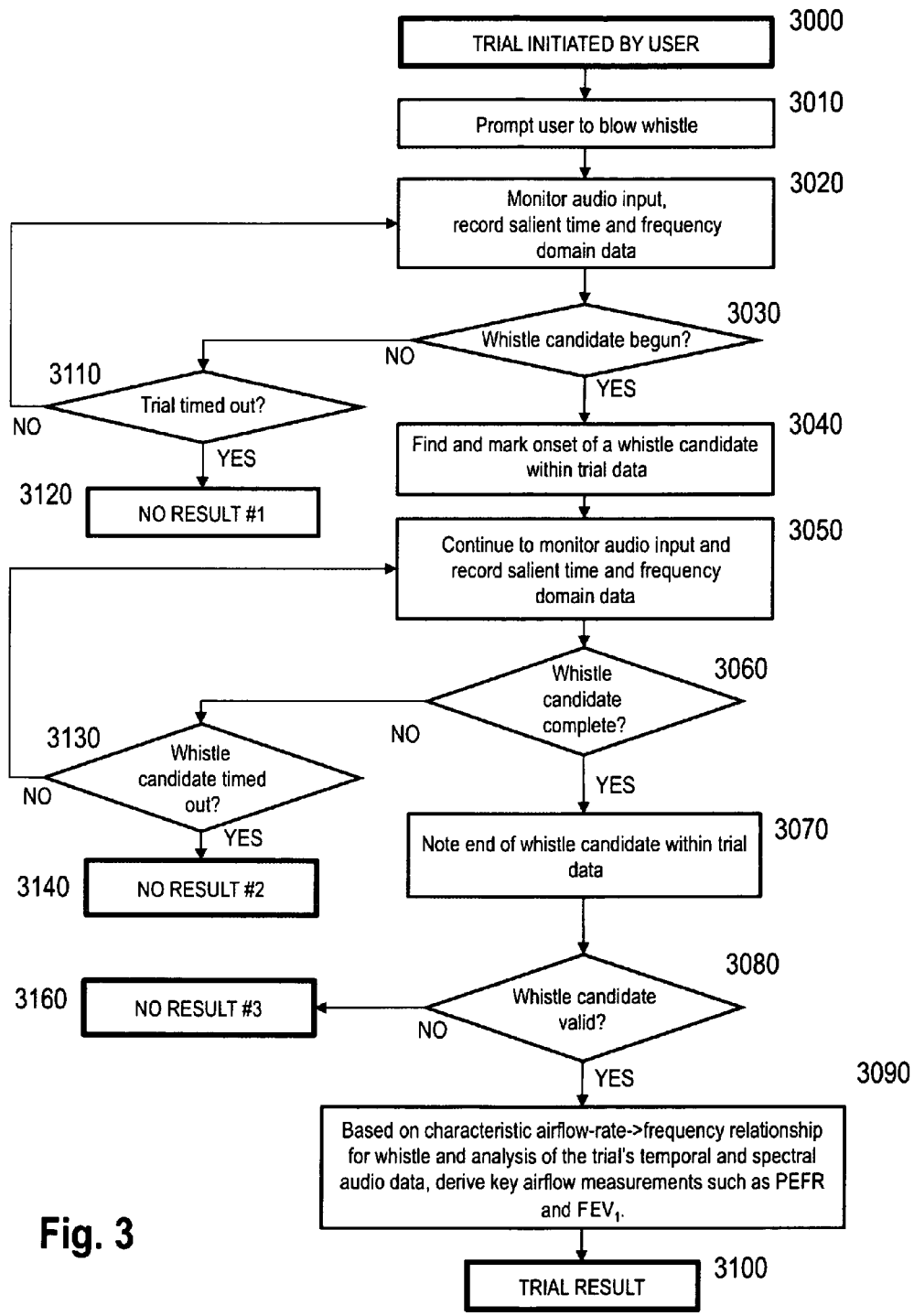
FIG. 3 shows a high-level flow chart of a software process, in accordance with one or more embodiments.

FIG. 3 shows a software process. In one or more embodiments of the present invention, this software process executes on a hand-held mobile digital device with audio input and networking capabilities (such as a mobile phone, personal digital assistant, mobile gaming system, or tablet). The stages of the software process are as follows:

In stage 3000 the software process is initiated by manual user input (such as pressing a button—or a virtual touchscreen button—on the mobile device).

In stage 3010, the software process communicates to the user that it is ready to receive audio input (in other words, that it is ready for the user to blow the whistle).

In stage 3020, the process monitors audio input, and records time and frequency-domain audio data in preparation for determining whether the onset of a "whistlesound candidate"—a sound that might prove to be a valid whistle sound—has begun.

In stage 3030 the process determines, based on recorded time and frequency-domain audio data, whether a whistle-sound candidate has begun.

In stage 3040, the process finds the onset of a whistle-sound candidate, and marks this onset within the data recorded for the current measurement trial.

In stage 3050, the process continues to monitor audio input and record relevant time and frequency-domain data.

In stage 3060, the software process determines whether a whistle-sound candidate has reached completion or timed out.

In stage 3070, the end of a whistle-sound candidate is noted with respect to the trial's recorded time and frequency-domain data.

Within stage 3080, the software process examines time and frequency-domain audio data corresponding to the duration between whistle-sound candidate onset and cessation, in order to assess whether the whistle-sound candidate represents a valid whistle sound.

In stage 3090, the software process maps frequency-domain audio data for a whistle sound to airflow rate measurements, based on the whistle's characteristic relationship between airflow rate and frequency. From these airflow rate measurements, the software process then derives key respiratory metrics such as PEFR and $FEV_1$.

In stage 3100, the software process arrives at results for the trial (including the key respiratory metrics determined in stage 3090) and makes these results accessible to entities outside of the software process, such as the user and other software processes.

In stage 3110, the software process determines whether a trial has continued for longer than a certain maximum allowed duration.

In stage 3120, the process communicates to the user that the trial has timed out before the onset of any whistle-sound candidate has been identified, and provides the user with relevant feedback of a corrective, instructional, and/or motivational nature.

In stage 3130, the software process determines whether a whistle-sound candidate has continued for longer than a certain maximum allowed duration.

In stage 3140, the process communicates to the user that the trial has timed out after the onset of a potentially valid whistle-sound, and provides the user with relevant feedback of a corrective, instructional, and/or motivational nature.

Figure 4:
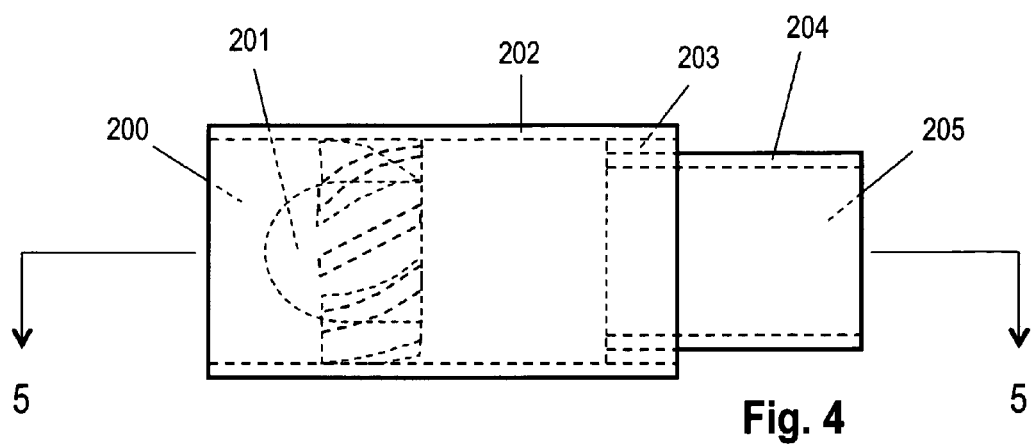
FIG. 4 shows a side view of a whistle, in accordance with one or more embodiments.
Figure 5:
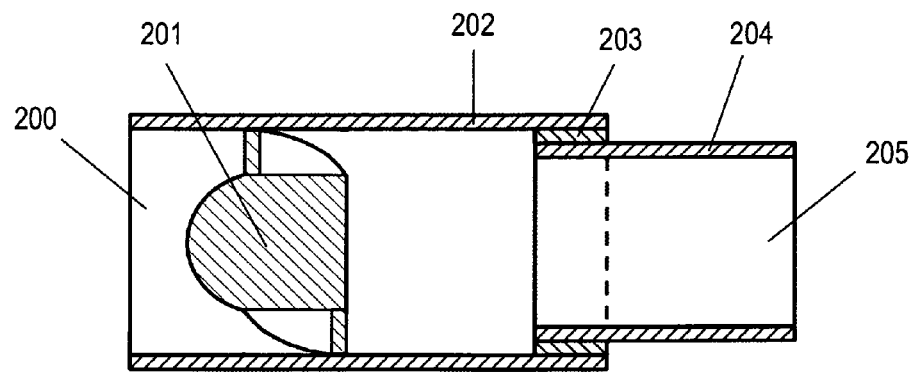
FIG. 5 shows a sectional side view of a whistle, in accordance with one or more embodiments.

FIG. 4 illustrates a side view of the whistle illustrated in FIG. 2, and indicates the cross section for the sectional view illustrated in FIG. 5. Apparent from FIG. 4 are airflow guide 201's rounded front portion and slanted vanes.

FIG. 5 illustrates a sectional view of the whistle illustrated in FIG. 2.

Figure 6:
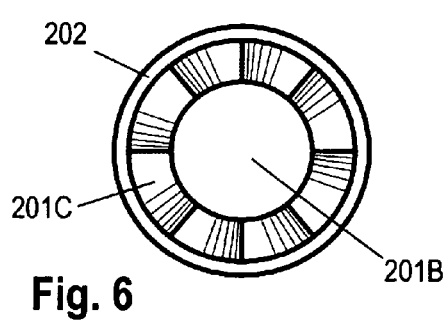
FIG. 6 shows a front view of a whistle, in accordance with one or more embodiments.

FIG. 6 illustrates a front view of the whistle illustrated in FIG. 2. Within FIG. 6, the vanes of the airflow guide—such as one vane referenced by 201C—are apparent. The front of the central portion of the airflow guide is referenced by 201B. The airflow guide's vanes and central portion, together with the inner wall of main tube 202, define a set of airflow passageways that wind around the central axis of the whistle's central cavity.

FIG. 7 depicts the characteristic relationship between airflow rate and audio frequency for one prototype whistle constructed according to FIG. 2. The relationship is experimentally derived from recorded audio and airflow rate data.

Audio data is sampled at 44.1 kHz, using a fast Fourier transform (FFT) of size 1024. Given this sampling rate and FFT size, the FFT frequency bin width is approximately 43 Hz. The presence of multiple data points at periodic audio frequency intervals is due to FFT frequency bin-width quantization.

Airflow rate is measured at a sampling rate of 83 Hz using a factory-calibrated differential-pressure pneumotachograph. The precision of the pneumotachograph measurements is believed to be within ±5 L/min.

Notably, whistle frequency remains comfortably within an audible range. The experimentally derived relationship between airflow rate and audio frequency is close to linear, and can be approximated by a second-order polynomial with $R^2=0.99866$.

FIG. 8 illustrates an alternate embodiment. The figure depicts a user 100 blowing through a whistle with a horn-shaped exterior 801 towards a hand-held mobile digital device 102.

OPERATION

FIGS. 1, 2, 3, 7—First Embodiment

Scenario 1: A Successful Measurement Trial

The user 100 initiates a measurement trial by starting the software process outlined in FIG. 3 on mobile device 102, then expresses to the process his or her intention to begin a new measurement trial by pressing a button on the mobile device. In 3010, the software process prompts the user to blow the whistle illustrated in FIG. 2, and begins to monitor and record audio input in 3020.

The user exhales forcibly through the inlet 200 of the whistle, generating an airflow that passes around the airflow guide 201 and through the set of airflow passageways formed by the airflow guide and the inner wall of main tube 202. As expiratory airflow passes through these airflow passageways, a vortex is generated within the whistle's central cavity. This vortex passes through the remaining stages of the whistle, and exits through the whistle's outlet 205. As the vortex exits the whistle's outlet, it begins to whip around the outlet tube's central axis with an angular velocity comparable to its rotational velocity, thus generating the whistle's characteristic sound.

Next, the software process identifies the onset of a "whistle-sound candidate"—a sound that may ultimately be determined by the software process to be a valid whistle-sound—in 3030. The software process marks the onset of the whistle-sound candidate within the trial data in 3040 while continuing to monitor and record audio in 3050.

As the user's forced exhalation finishes, the whistle's sound subsides. The software process identifies the end of the whistle-sound candidate in 3060, and marks the end of this whistle-sound candidate within recorded audio data in 3070. Based on data recorded between the start and end of the whistle-sound candidate, in 3080 the software process determines that the whistle-sound candidate represents a valid whistle-sound, and continues to stage 3090, in which the whistle-sound's audio frequency data is used—in conjunction with the whistle-device's characteristic relationship between airflow-rate and frequency—to derive measurements for PEFR and $FEV_1$. These results are subsequently made available to entities outside the software process, including the user and other software processes in 3100. Once results have been made available to the user and other software processes running on the mobile device, these results can be made available to remote digital devices and services (FIG. 1; 105, 106, 107) on one or more of the mobile device's network(s) for the purposes of informing family members 103 and physicians 104, and maintaining a secure and accessible record of completed trials.

Scenario 2: A Trial Times Out Before a Whistle-Sound Candidate has Begun

In the event that a user initiates a trial (FIG. 3, 3000), but the software process does not identify the onset of a whistlesound candidate within a maximum time period, the trial times out, as detected within 3110. After timing out, the trial communicates to the user that it has timed out in stage 3120, and offers relevant recommendations on how to avoid timing out during future trials.

Scenario 3: A Trial Times Out after a Whistle-Sound Candidate has Begun

In the event that the software process identifies the onset of a whistle-sound candidate, but does not identify cessation of the whistle-sound candidate within a certain maximum allowable duration, the trial times out, as detected within 3130. After timing out, the trial communicates to the user that it has timed out in stage 3140, and offers relevant recommendations on how to avoid timing out during future trials.

Scenario 4: A Whistle-Sound Candidate is Determined Invalid

In the event that the software process identifies the onset and cessation of a whistle-sound candidate, the software process proceeds to 3080 to determine whether or not the candidate represents a valid whistle-sound. If the data for the candidate does not meet criteria required for a valid whistle-sound, the software process passes to stage 3160, and offers relevant recommendations for how to improve the chances of completing successful trials in the future.

DISCUSSION OF ALTERNATIVE EMBODIMENTS

FIGS. 8, 9, 10

Details of embodiments of the present invention may vary considerably without departing from the basic principle of the present invention.

Further refinements made for engineering, industrial design, interaction design and standards-conformance purposes may change proportions, dimensions, time-out durations, and numerous other characteristics. Within the whistle depicted in FIGS. 2, 4, 5 and 6, for example, the number, angle, curvature and shape of its airflow guide's vanes 201C may change. Instead of vanes, a helical set of holes may be employed to guide airflow into a spiraling motion.

Figure 9:
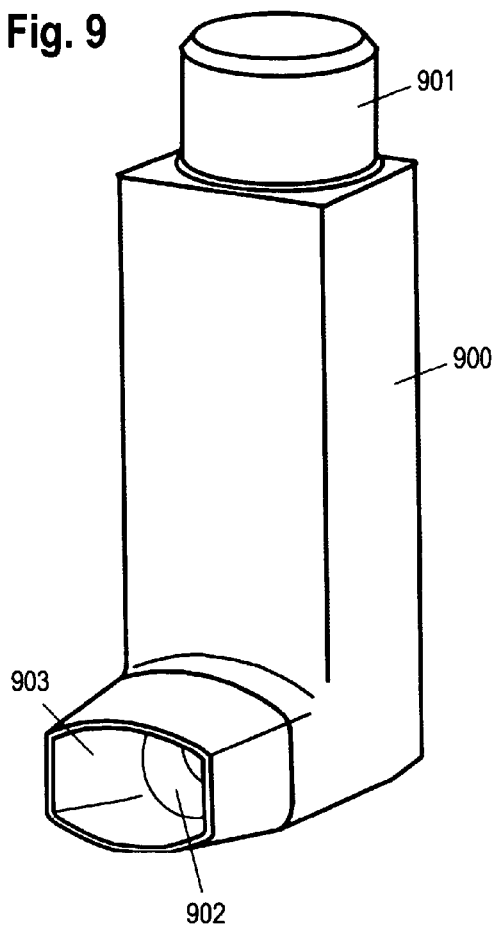
FIG. 9 depicts a perspective view of a whistle combined with a medicine dosage dispenser, in accordance with one or more embodiments.
Figure 10:
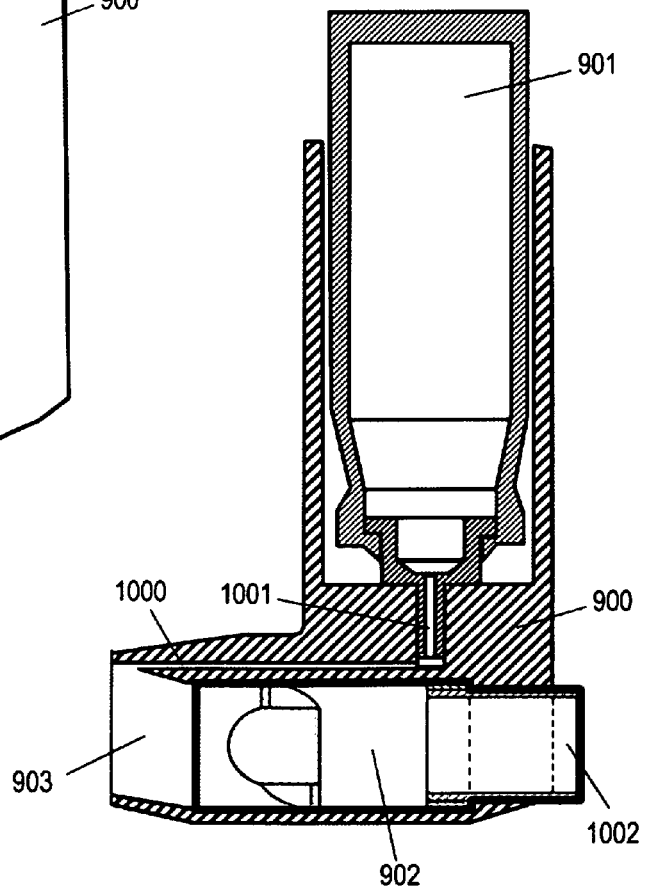
FIG. 10 shows a sectional view of the combination of whistle and medicine dosage dispenser depicted in FIG. 9.

According to one or more additional alternate embodiments, the whistle may include a medicine dosage dispenser to reduce the total number of asthma management-related items a patient must carry on his or her person. FIGS. 9 and 10 show one variation of a combined whistle-dispenser. This variation includes a housing 900, a recess for holding a standard medicine container 901, and a whistle 902 similar to the previously discussed whistle depicted in FIG. 2. The depicted combination whistle-dispenser further comprises a delivery channel for medication 1000 that connects the medicine container's nozzle 1001 with the whistle-dispenser's mouthpiece 903. Airflow entering the mouthpiece passes through the whistle and out an airflow outlet 1002.

When the medicine container is pushed into its recess, a dosage of medicine is dispensed through the whistle-dispenser's mouthpiece. When a user exhales forcefully through the whistle-dispenser's mouthpiece, all expiratory airflow passing through the mouthpiece passes through the whistle, and contributes to the generation of sound.

According to one or more alternate embodiments of the invention, the external form of some variations of the whistle could resemble brass or woodwind musical instruments. For example, FIG. 8 depicts a user 100 blowing through horn-shaped whistle 801 towards a hand-held mobile digital device 102, thereby recasting the task of routine peak flow measurement in terms of a potentially more enjoyable performance-like activity.

An integrated or detachable cap could cover the inlet region of some alternative variations of the whistle, to keep the inlet region clean. The action of capping the inlet could be designed so as to have the effect of wiping the inlet region clean. The outlet tube could be designed to "collapse" into the main tube when the whistle is not in use, in order to support a solution that is more compact.

Alternative variations of the whistle could incorporate an identification code that, when submitted to a specified information service via a mobile device, returns a message validating a whistle's authenticity—to discourage counterfeiting, and thereby promote safety and reliability.

Just as the present invention's scope permits extensive variation of the whistle, it also permits extensive variation of the software process. Alternative variations of the software process could execute remotely, on a networked resource such as 105 with access to audio data from a mobile digital device, or in distributed fashion: partially on the mobile device, and partially over a network to which the mobile device connects.

Instead of monitoring for one and only one whistle sound as outlined in FIG. 3, alternate implementations of the software process could monitor continually for the occurrence of whistle-sound candidates.

Alternate variations of the software process could be structured such that the recording of audio data occurs within an interrupt service routine or a separate software thread, rather than in one main routine as FIG. 3 depicts.

Still other variations of the software process could provide the user with real-time interactive feedback while the user is blowing through the whistle.

Such alternate embodiments of the present invention's whistle and software process are offered as examples to illustrate breadth of scope; numerous substitutions and variations are possible without altering the basic premise of the invention.

ADVANTAGES

From the previous description, a number of advantages of one or more embodiments of the present invention become evident:

(a) Embodiments of the present invention enable leveraging the prodigious capabilities of prevalent hand-held mobile digital devices equipped with audio input (such as mobile phones, personal digital assistants, mobile gaming platforms and tablets), while simultaneously simplifying requirements for—and reducing the cost of—a dedicated portable spirometry appliance.

(b) Embodiments of the present invention render respiratory measurements digitally accessible to hand-held mobile digital devices in a manner that is wireless, requires no electric power for signal transmission, and requires no wireless network configuration.

(c) Whistle variations within more than one embodiment of the present invention intrinsically provide a user with audible real-time feedback that can serve to motivate the user to give his or her best effort, and thus indirectly contribute to the accuracy of spirometric measurements.

(d) Whistle variations within one or more embodiments of the present invention are compact, highly portable, and contain no moving parts, electronics or batteries.

(e) Because whistle variations within one or more embodiments of the present invention can be made from a single non-toxic material and contain no electronics, they can be manufactured using less energy and materials than alternate solutions, and can be recycled more easily.

(f) Because whistle variations within one or more embodiments of the present invention can be manufactured from one non-toxic substance, they can be designed so as not to put toxic substances in close proximity with the entranceways of a user's respiratory and digestive tracts.

(g) Whistle variations within one or more embodiments of the present invention can be designed to accommodate the frequency limitations of the microphones used in hand-held mobile digital devices, as well as the bandwidth limitations of some of the wireless networks to which hand-held mobile digital devices typically connect. As a result, airflow measurements can be derived by variations of the software process running locally on a hand-held mobile digital device, as well as by variations of the software process running remotely, on another device connected to a network to which the hand-held mobile digital device connects.

(h) In contrast with vortex whistles that position inlet and outlet at right angles relative to each other, whistle variations within more than one embodiment of the present invention align the direction of incoming airflow with the central axis of the outlet. Such an alignment assists a user to aim (and feel like they are aiming) at a hand-held mobile digital device, permits the user to easily view interactive graphical feedback from the device, and supports reliable communication between whistle and mobile digital device.

(i) In contrast with some other spirometry solutions, embodiments of the present invention require no frequent calibration.

(j) Since whistle variations within embodiments of the present invention contain no electronics, they can be cleaned with readily available aqueous solutions without risk of damage.

CONCLUSIONS, RAMIFICATIONS, AND SCOPE

Accordingly, the reader will see that at least one embodiment of the present invention enables a more versatile expiratory measurement solution that is amenable to improved communication, visualization, reminding, annotation, correlation and motivation at less additional expense to a user, through leveraging the capabilities of ubiquitous hand-held mobile digital devices with audio input and networking capabilities (such as mobile phones, personal digital assistants, mobile gaming platforms, and tablets).

Though the description above contains specificities, these specificities should not be construed as limiting the scope of embodiments, but merely as assisting in the presentation of illustrative examples. Additional variations are possible; for example, alternate variations of the whistle could incorporate a fixture and/or holes that enable the whistle to be worn using a strap or a necklace, or alternatively, used as part of a keychain. Alternate variations of the system's software process could automatically monitor for several trials in succession, rather than just one trial.

Thus, the scope of the embodiments should be determined by the appended claims and their legal equivalents, rather than by any specific examples given.

I claim:

1. A method for spirometric measurement using a whistle that has a pre-determined correlation between through-flowing airflow per unit time and frequency of acoustic emissions from the whistle, and a mobile digital device with a microphone, a sampling capability, a display, a data recording, processing and storage capability, and an ability to communicate data over a wireless network with an external data processing and storage resource, the whistle being physically separate from the mobile digital device and capable of transmitting an audio signal through electrically passive means for reception by the microphone of the mobile digital device, the method comprising:

recording samples of an audio signal in an audible frequency range received at the microphone of the mobile digital device using the sampling capability of the mobile digital device, determining frequency values of the audio signal based on said recorded samples, determining whether the audio signal received at the microphone of the mobile digital device corresponds to an audio signal transmitted by the whistle in response to a user performing an exhalation forcefully through said whistle based on at least one of time-domain data and the determined frequency values of the audio signal, determining at least one expiratory airflow rate value of the user based on said determined frequency values and said correlation, determining at least one respiratory parameter of the user based on said at least one expiratory airflow rate value, and presenting feedback to said user on the display of the mobile device, wherein the feedback is based on at least one of the following: at least one of said recorded audio samples, at least one of said determined frequency values, said at least one determined expiratory airflow rate value, and said at least one determined respiratory parameter, wherein at least one of the steps of determining at least one expiratory airflow rate value of the user, determining at least one respiratory parameter of the user and presenting feedback to said user on the display of the mobile device is performed in response to determining that the audio signal received at the microphone of the mobile digital device corresponds to an audio signal transmitted by the whistle in response to a user performing an exhalation forcefully through said whistle, and wherein the steps of determining frequency values, determining at least one expiratory airflow rate value and determining at least one respiratory parameter are each performed by at least one of the mobile digital device and the external data processing and storage resource.

2. The method of claim 1, wherein said at least one respiratory parameters comprises at least one of PEFR and $FEV_1$.

3. The method of claim 1, wherein the steps of recording samples, determining frequency values, determining at least one expiratory airflow rate value and determining at least one respiratory parameter are performed on said mobile digital device.

4. The method of claim 1, wherein at least one the steps of determining frequency values, determining at least one expiratory airflow rate value and determining at least one respiratory parameter are performed by said external data processing and storage resource, accessed through said mobile digital device.

5. The method of claim 1, wherein said mobile digital device is a mobile phone, personal digital assistant, tablet, or mobile gaming platform.

6. The method of claim 1, wherein the step of determining frequency values occurs during said user's exhalation.

7. The method of claim 1, wherein the step of determining expiratory airflow rate values occurs once said user's exhalation is determined to be complete.

8. The method of claim 6, wherein presenting feedback to said user comprises presenting feedback to said user on the display of the mobile digital device during said exhalation through said whistle, wherein said feedback is based on at least one of the following: at least one of said recorded audio samples, at least one of said determining frequency values, at least one of said determined expiratory airflow rate values, and said at least one determined respiratory parameter.

9. The method of claim 1, wherein presenting feedback to said user comprises presenting feedback to said user on the display of the mobile digital device once said user's exhalation is determined to be complete, wherein said feedback is based on at least one of the following: at least one of said recorded audio samples, at least one of said determined frequency values, said at least one determined expiratory airflow rate value, and said at least one determined respiratory parameter.

10. The method of claim 1, further comprising:
   transmitting at least one of the following to an external processing and storage resource via the wireless network: at least one of said recorded audio samples, at least one of said determined frequency values, said at least one determined expiratory airflow rate value, and said at least one determined respiratory parameter.

* * * * *